United States Patent
Kiesele et al.

[11] Patent Number: 5,879,527
[45] Date of Patent: Mar. 9, 1999

[54] FILTER FOR AN ELECTROCHEMICAL MEASURING CELL

[75] Inventors: Herbert Kiesele; Frank Mett, both of Lübeck, Germany

[73] Assignee: Drägerwerk Aktiengesellschaft, Lubeck, Germany

[21] Appl. No.: 636,639

[22] Filed: Apr. 23, 1996

[30] Foreign Application Priority Data

May 10, 1995 [DE] Germany .................. 195 17 144.6

[51] Int. Cl.[6] .................. G01N 27/28; G01N 27/404
[52] U.S. Cl. .................. 204/431; 96/135; 204/276; 204/415
[58] Field of Search .................. 204/276, 415, 204/431, 432; 96/134, 135

[56] References Cited

U.S. PATENT DOCUMENTS

| | | | |
|---|---|---|---|
| 2,638,179 | 5/1953 | Yard | 96/134 |
| 3,854,912 | 12/1974 | Terrell et al. | 96/134 |
| 3,911,080 | 10/1975 | Mehl et al. | 96/134 |
| 4,141,800 | 2/1979 | Breuer et al. | 204/415 |
| 4,457,843 | 7/1984 | Cullen et al. | 96/108 |
| 4,591,423 | 5/1986 | Kato et al. | 204/428 |
| 4,624,770 | 11/1986 | Yamada et al. | 204/428 |
| 4,633,704 | 1/1987 | Tantram et al. | 204/415 |
| 4,830,643 | 5/1989 | Sassa et al. | 96/108 |
| 5,300,139 | 4/1994 | Lin | 96/135 |

FOREIGN PATENT DOCUMENTS

| | | |
|---|---|---|
| 0 016 423 A1 | 3/1980 | European Pat. Off. . |
| 34 45 638 C2 | 4/1987 | Germany . |
| 27 09 903 C2 | 5/1988 | Germany . |

*Primary Examiner*—T. Tung
*Attorney, Agent, or Firm*—McGlew and Tuttle

[57] ABSTRACT

A filter for an electrochemical measuring cell with a filter housing and a filter material contained therein is improved, with a simple design, such that interfering gas components cannot reach the measuring cell from the gas mixture. This is accomplished by the filter housing being formed of a porous, gas-permeable material.

20 Claims, 3 Drawing Sheets

FILTER FOR AN ELECTROCHEMICAL MEASURING CELL

FIELD OF THE INVENTION

The present invention pertains to a filter for an electrochemical measuring cell and more particularly to an electrochemical measuring cell with a filter and with a filter housing.

BACKGROUND OF THE INVENTION

The state of the art shows various suggestions for equipping electrochemical measuring cells such that controlled diffusion conditions are preset for the detection of a defined gas component in a gas mixture, i.e., e.g., of CO in its mixture with $H_2S$, on the one hand, and that the retention of "interfering" gas components, i.e., e.g., $H_2S$, is ensured, on the other hand.

On the one hand, so-called diffusion diaphragms, which are described in, e.g., EP 0016423 A1 and are to contribute to the optimization of the electrochemical measurement conditions, have been known for limiting the access of a gas component to be detected to the measuring cell. On the other hand, filters are inserted between the gas mixture and the measuring cell proper in order to retain, e.g., moisture, dust or especially also gas components which interfere with the measurement from the mixture and which would otherwise distort the measured signal of the measuring cell. A gas-measuring apparatus with a diffusion barrier with a capillary is disclosed in DE 27 09 903 C2.

The provision of a filter layer in the gas inlet for separating moisture for a calorimetric gas dosimeter is described in DE 34 45 638 C2.

The commercially available filters are either rigidly connected to the measuring cell and are not replaceable, or they cause interference signals due to leakage flows through the "bypass" between the filter housing and the measuring cell proper. These leakage flows are due to the fact that the filters are not fitted into the housing of the measuring cell in an absolutely gas-tight manner, and it is therefore hardly possible to prevent interfering gas components from flowing directly through this air gap because of the existing potential gradient and from reaching the measuring cell without flowing through the filter material and from causing an interference signal there.

SUMMARY AND OBJECTS OF THE INVENTION

The primary object of the present invention is to suggest a filter for electrochemical measuring cells, which has a simple design and extensively ensures that interfering gas components cannot enter the measuring cell from the gas mixture.

This object is accomplished by the filter housing comprising a porous, gas-permeable material. The filter housing of porous gas permeable material preferably comprises a lower, pot-shaped element and an upper element in the form of a closing cover. The closing cover is preferably provided on the outside with a gas-impermeable diffusion diaphragm with passage openings which may be designed as a plurality of slots.

The wall thickness of the filter housing is preferably from 0.5 to 1.5 mm. A sealant for connecting the pot-shaped element to the cover in a gas-tight manner is preferably arranged between the top edge of the pot-shaped element and the outer, lower edge area of the cover.

It was surprisingly found that the interfering gas components which usually reach the measuring cell directly as a bypass flow through the air gap between the measuring cell and the filter housing can be captured practically completely with a filter housing made of a porous, gas-permeable material with a filter material located in it, which selectively binds the interfering gas component. This happens due to the fact that the air gap between the measuring cell and the filter housing is "chemically evacuated" through the filter material, because the wall is permeable to gases and the interfering gas component flows into the interior of the housing radially to the filter material, corresponding to the radial concentration gradient, and it is selectively bound there. The longer the flow path h of the gas in parallel to the housing wall and the smaller the wall thickness d of the housing, the greater is the effect of the radial flow through the housing wall. It was found to be advantageous for this h:d ratio to be at least 3 and especially greater than 5. The material of the housing should preferably consist of a uniformly porous, hydrophobic and chemically resistant material which is permeable to the interfering gas components. The materials suitable for this purpose include, e.g., sintered materials. Polytetrafluoroethylene (PTFE) proved to be particularly suitable. The filter material is usually used in the granular form, and it contains substances which selectively bind the interfering gas component. These filter materials can be called sorption filter materials and have been known from the state of the art. A filter according to the present invention will be described below on the basis of an exemplary embodiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
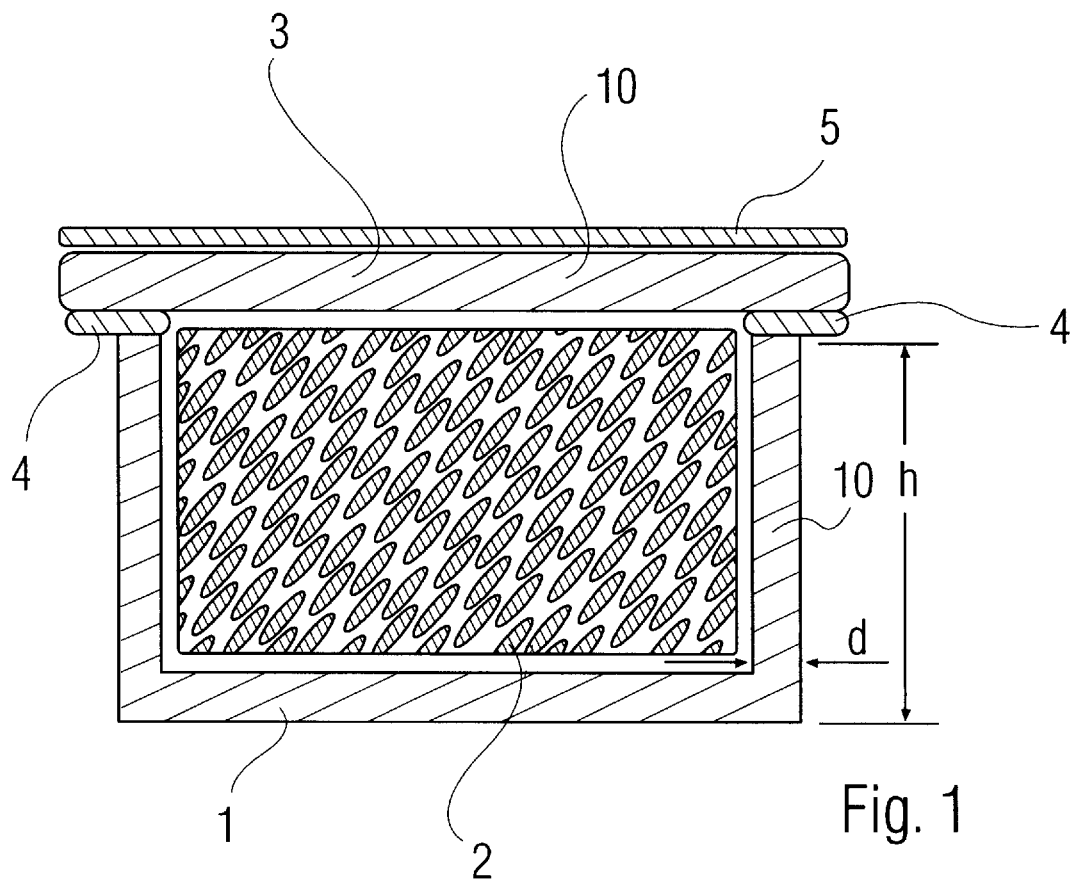
FIG. 1 is a central longitudinal sectional view through a cylindrical filter.

The cylindrical filter shown comprises a filter housing 10 made of porous, gas-permeable PTFE and the filter material 2 contained therein, pressed as a filter tablet in the shape of a disk from PTFE powder in the example, together with a substance selectively binding the interfering gas components. The filter housing has a wall thickness d of about 1 mm and comprises a lower, pot-shaped element 1 and an upper element in the form of a closing cover 3, which has a somewhat larger diameter here than the pot-shaped element 1 and projects radially. The cover 3 is connected to the element 1 by a sealant 4 in a gas-tight manner. The sealant 4 may consist of, e.g., a silicone layer or a welded polyethylene film. The task of the sealant 4 is to bring about a barrier action for an interfering gas component penetrating from the top (i.e., from the outside): The filter shown is inserted, e.g., as an insert into the accommodating space of an electrochemical measuring cell. The gas mixture to be measured is located, corresponding to FIG. 1, above the cover 3, while the measuring cell radially surrounds the lower, pot-shaped element 1 up to the level of the sealant 4, optionally including the cover 3, so that the measuring cell and the filter are flush with one another. As a result, the filter is reversibly inserted into the measuring cell and can be replaced when needed. A diffusion diaphragm 5 in the form of a welded-on or adhered gas-impermeable foil or film, which contains passage openings 6, e.g., in the form of slots, is placed on the top side of the cover 3. The suitable materials include, e.g., metal foils or plastic films. Depending on the dimensioning of the measuring cell and the measurement conditions, the number, the size and the distribution pattern of the passage openings 6 are used to control the diffusion of the gas into the filter and into the electrochemical measuring cell, not shown in FIG. 1, and ultimately the measurement proper. The diffusion diaphragm 5 may be labeled, depending on the specification, by corresponding markings or colors for the particular intended use for which it is suitable, and it can be correspondingly replaced by the user. It is desirable, in general, to achieve the most uniform gas flow possible over the flow cross section in order to admit the gas uniformly to the measuring cell. It was found that an interfering gas component usually flowing directly to the measuring electrode in the air gap between the housing wall and the measuring cell is deflected practically completely in the radial direction of flow toward the filter material 2 if the flow path of the gas along the housing is at least about 3 to 5 times the flow path radially through the housing wall. This deflection, which is a radial deflection in this case, in the direction of the filter material, follows from the concentration gradient in the direction of the filter material 2 and from the possibility of the passage of gas through the porous, gas-permeable filter housing 10. In contrast, the gas component to be detected, e.g., CO, can also flow directly toward the measuring electrode through the porous housing wall due to diffusion, so that the sensitivity of the measuring cell is increased as a whole and interfering storage effects due to amounts of gas not having flown off are reduced. The diameter of the element 1 in the example is 12 mm, its height h is 6 mm, and the circumferential projection of the cover 3 is about 1 mm.

Figure 2:
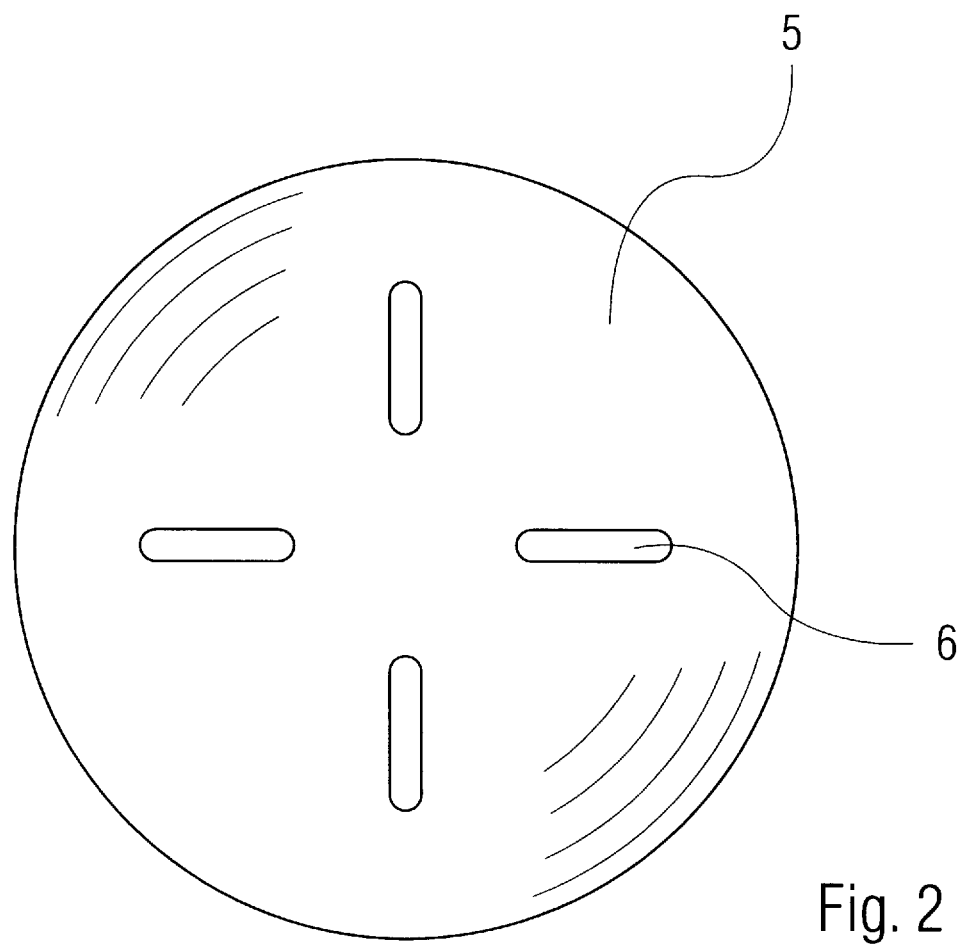
FIG. 2 is a top view of the filter according to FIG. 1.
Figure 3:
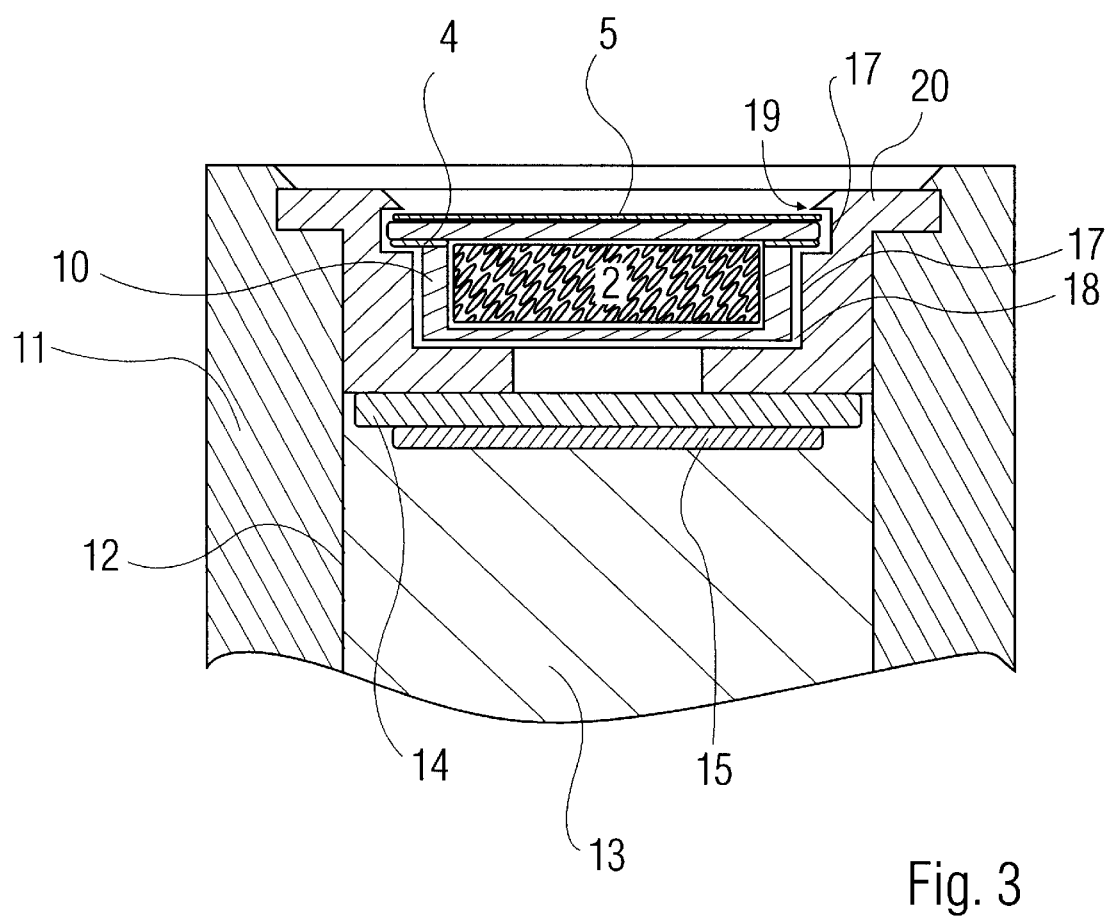
FIG. 3 is a longitudinal sectional view through an electrochemical measuring cell.

FIG. 3 shows a longitudinal section through an electrochemical measuring cell 11 with the filter housing 10 according to the present invention. Identical components are designated with the same reference numbers as in FIGS. 1 and 2. The electrochemical measuring cell 11 shown schematically has an electrolyte space 12, which is filled with an electrolyte 13 and is separated with a diffusion diaphragm 14 toward the gas component to be detected, and has a measuring electrode 15 and a counterelectrode, not shown in FIG. 3. A pot-shaped holder 17 with snap-in tongues 20 for accommodating the filter housing 10 is provided in the electrochemical measuring cell 11 above the diffusion diaphragm 14. A gas component, which enters an air gap 18 between the filter housing 10 and the holder 17 and is schematically indicated by an arrow 19, flows into the interior of the filter housing 10, corresponding to the radial concentration gradient, as a result of which the air gap is "chemically evacuated." It is therefore possible to omit an expensive sealing of the filter housing 10 against the electrochemical measuring cell 11 in the area of the snap-in tongues 20.

While a specific embodiment of the invention has been shown and described in detail to illustrate the application of the principles of the invention, it will be understood that the invention may be embodied otherwise without departing from such principles.

What is claimed is:

1. A filter and electrochemical measuring cell, comprising:
   a measuring cell housing including cell walls with an open end;
   electrochemical measuring means disposed in said measuring cell;
   a filter housing;
   a filter material contained within said housing, said filter housing being formed of a porous, gas-permeable material, said filter housing being disposed adjacent said open end of said cell supported by said cell walls, said porous, gas-permeable material having an outer surface, said cell walls and said outer surface of said gas-permeable material cooperating to define a gap whereby interfering gas components entering said gap are deflected radially toward said filter housing and are prevented from bypassing said filter housing and entering said cell, even without a seal provided between said filter housing and said cell walls.

2. A filter according to claim 1, wherein said porous, gas-permeable material is a polytetrafluoroethylene.

3. A filter according to claim 1, wherein said filter housing comprises a lower, pot-shaped element and an upper element defining a closing cover.

4. A filter according to claim 3, wherein said closing cover is provided on an outside with a gas-impermeable diffusion diaphragm, said diffusion diaphragm having passage openings allowing gas to pass therethrough.

5. A filter according to claim 4, wherein said passage openings are formed as a plurality of slots.

6. A filter according to claim 3, wherein a ratio of a height H of said pot-shaped element to a wall thickness D of said pot-shaped element is at least 3, and said height H substantially defines a length of said gap.

7. A filter according to claim 3, further comprising a sealant for connecting said pot-shaped element to said closing cover in a gas-tight manner, said sealant being arranged between a top edge of said pot-shaped element and an outer, lower edge of said cover.

8. A filter according to claim 3, wherein said pot-shaped element is formed of a wall with a thickness D of from 0.5 to 1.5 mm and a ratio of a height H of said pot-shaped element wall to the wall thickness D of said pot-shaped element is greater than or equal to 3, and said height H substantially defines a length of said gap.

9. A filter according to claim 8, wherein said ratio is greater than 5.

10. A filter according to claim 1, wherein said housing has a wall thickness of from 0.5 to 1.5 mm.

11. An electrochemical measuring cell, comprising:
    a cell housing including cell walls with an open end;
    a pot-shaped holder disposed at said open end, said pot shaped holder defining a receiving space;
    a filter housing comprising a pot-shaped element and a closing cover, said filter housing having filter material disposed therein, said filter housing being formed of a porous, gas-permeable material, said filter housing being disposed in said receiving space defining an air-gap between said filter housing and said pot-shaped holder, whereby interfering gas components entering said gap are deflected radially toward said filter housing and are prevented from bypassing said filter housing and entering said cell, even without a seal provided between said filter housing and said cell walls.

12. A filter according to claim 11, wherein said porous, gas-permeable material is polytetrafluoroethylene.

13. A filter according to claim 12, wherein said closing cover is provided on an outside with a gas-impermeable diffusion diaphragm, said diffusion diaphragm having passage openings allowing gas to pass therethrough.

14. A filter according to claim 13, wherein said passage openings are formed as a plurality of slots.

15. A filter according to claim 11, wherein said housing has a wall thickness of from 0.5 to 1.5 mm.

16. A filter according to claim 11, wherein a ratio of a height H of said pot-shaped element to a wall thickness D of said pot-shaped element is at least 3.

17. A filter according to claim 11, further comprising a sealant for connecting said pot-shaped element to said closing cover in a gas-tight manner, said sealant being arranged between a top edge of said pot-shaped element and an outer, lower edge of said cover.

18. A filter according to claim 11, wherein said pot-shaped element is formed of a wall with a thickness D of from 0.5 to 1.5 mm and a ratio of a height H of said pot-shaped element wall and the wall thickness D of said the pot-shaped element is greater than or equal to 3, and said height H substantially defines a length of said gap.

19. A filter according to claim 18, wherein said ratio is greater than 5.

20. A filter and electrochemical measuring cell, comprising:

a measuring cell housing including cell walls with an open end;

electrochemical measuring means material disposed in said measuring cell;

a filter housing;

a filter material contained within said housing, said filter housing being formed of a porous, gas-permeable material, said filter housing being disposed adjacent said open end of said cell supported by said cell walls, said porous, gas-permeable material having an outer surface, said cell walls and said outer surface of said gas-permeable material cooperating to define a gap, whereby interfering gas components entering said gap are deflected radially toward said filter housing and are prevented from bypassing said filter housing and entering said cell, said gap extending uninterrupted from a gas entry side of said filter housing to an intake opening within said cell.

* * * * *